United States Patent [19]

Evans et al.

[11] Patent Number: 5,498,625
[45] Date of Patent: Mar. 12, 1996

[54] SUBSTANTIALLY PURE ENANTIENERS OF 2-AZABICYCLO(2.2.1)HEPT-5-EN-3-ONE

[75] Inventors: Christopher T. Evans, Heydon; Stanley M. Roberts, Kenton, both of England

[73] Assignee: Chiroscience Limited, Cambridge, England

[21] Appl. No.: 336,754

[22] Filed: Nov. 8, 1994

Related U.S. Application Data

[60] Continuation of Ser. No. 35,236, Mar. 22, 1993, abandoned, which is a division of Ser. No. 596,306, Oct. 19, 1990, Pat. No. 5,284,769.

[30] Foreign Application Priority Data

Oct. 16, 1989 [GB] United Kingdom ............... 8923278
Oct. 27, 1989 [GB] United Kingdom ............... 8924209
Jan. 17, 1990 [GB] United Kingdom ............... 9000995

[51] Int. Cl.$^6$ ............... A01N 43/38; C07C 7/00; C12N 9/78; C07D 207/12
[52] U.S. Cl. ............... 514/412; 435/121; 435/128; 435/136; 435/147; 435/227; 435/280; 514/408; 514/418; 514/419; 514/676; 514/740; 548/543
[58] Field of Search ............... 514/659, 412, 514/408, 418, 419, 676, 740; 548/543; 435/121, 128, 136, 147, 227, 280

[56] References Cited

PUBLICATIONS

Ikbal et al., Eur. J. Med. Chem., 24, 1989, 415–20.
Caamano et al., Heterocycles, vol. 27, No. 12, 1988, pp. 2839–2841.
Chemical Abstracts, vol. 93, No. 3, Jul. 21, 1980, p. 738, abstract No. 26739t, Columbus, OH; R. D. Allan et al.: "Synthesis of analogs of GABA. III. All four stereoisomers of 3–aminocyclopentanecaroxylic acid and a stereochemical correlation with amidinomycin", Aust. J. Chem., 1979, 31(11), 2517–21.
R. D. Allan et al.: "N–Synthesis of Analogues of GABA. XV, Preparation and Resolution of Some Potent Cyclopentene and Cyclopentane Derivatives", Australian Journal of Chemistry, 1986, 39(6), 855–864.
Chemical Abstracts, vol. 91, No. 25, Dec. 17, 1979, p. 25, abstract no. 204205j, Columbus, OH; G. A. R. Johnston et al.: "Stereospecific actions of GABA analogs", and ADV Pharmacol Ther., Proc. Int. Congr. Pharmacol, 7th 1978 (Pub. 1979) 2, 11–18.
Journal of Organic Chemistry, vol. 43, No. 12, Jun. 9, 1978, pp. 2311–2320, American Chemical Society, Washington, D.C., S. Daluge et al.: "Synthesis of carbocyclic aminucleosides".
Evans et al., J. Chem. Soc. Perkin Trans. 1:656–657, 1991.

*Primary Examiner*—David M. Naff
*Assistant Examiner*—Michael V. Meller
*Attorney, Agent, or Firm*—Foley & Lardner

[57] ABSTRACT

Lactams of 1-amino-3-carboxylic acid cyclic compounds are produced in enantiomeric form, together with an enantiomer of the corresponding ring-opened amino-acid or ester, by reaction of the racemic lactam with a novel lactamase. The products are useful in the synthesis of chiral carbocyclic nucleotides. The enantiomer is preferrably 2-azabicyclo(2.2.1)hept-5-en-3-one. It is desirable to isolate the enantiomer comprising predominantly the (+) enantiomer and a residual amount of the (–) enantiomer, wherein the (+) enantiomer is present in an enantiomeric excess of at least about 88% over the (–) enantiomer or the enantiomer comprising predominantly the (–) enantiomer and a residual amount of the (+) enantiomer, wherein the (–) enantiomer is present in an enantiomeric excess of at least about 98% over the (+) enantiomer.

19 Claims, No Drawings

SUBSTANTIALLY PURE ENANTIENERS OF 2-AZABICYCLO(2.2.1)HEPT-5-EN-3-ONE

This application is a continuation of application Ser. No. 08/035,236, filed Mar. 22, 1993 now abandoned, which is a division of Ser. No. 07/596,306, filed Oct. 15, 1990, now U.S. Pat. No. 5,284,769.

FIELD OF THE INVENTION

This invention relates to chiral compounds having utility as intermediates in the synthesis of anti-viral agents, and to a process for their preparation.

BACKGROUND OF THE INVENTION

Various 9-substituted purines are known as anti-viral and anti-neoplastic agents. One such compound, known as AZT, has been used for the treatment of AIDS. More recent examples are disclosed in EP-A-4268672, U.S. Pat. No. 4,742,064, and also in GB-A-2217320 which, by way of specific illustration, describes a compound known as Carbovir (carbocyclic 2',3'-didehydro-2',3'-dideoxyguanosine). Not surprisingly, the enantiomers of such chiral compounds have different activities.

Carbovir and known analogues are prepared from the known γ-lactam, 2-azabicyclo[2.2.1]hept-5-en-3-one, i.e. the compound of formula

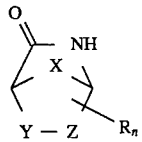

I in which X is —CH$_2$—, —Y—Z— is —CH=CH—, and R$_n$ is absent. The prior art indicates that the final product, or any intermediate or starting material, may be resolved by known methods, and that a racemic mixture of the product may be enzymatically converted to chirally pure compounds. The γ-lactam can be prepared by reacting cyclopentadiene with tosyl cyanide.

R. D. Allan et al, Eur. J. Pharmacol. 122 (1986) 339–348, disclose a series of GABA analogues, resolved and unresolved, including compounds of formula II

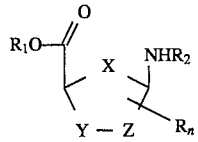

II in which —X— is —CH$_2$—, —Y—Z— is —CH=CH—, and R$_1$ and R$_2$ are H. In particular, (+)-1R,4R-4-aminocyclopent-2-ene-1-carboxylic acid is disclosed, although its activity is much lower than that of the structurally-isomeric 1-ene.

SUMMARY OF THE INVENTION

The present invention is based on the surprising discovery of lactamases that will react with a γ-lactam of formula I to give a single enantiomer of the lactam and the corresponding ring-opened compound of formula II in an enantiomeric form. The enantiomers are novel compounds, and are excellent synthons for a desired enantiomer of Carbovir or a pharmacologically-active analogue.

In compounds of the invention, X is —CH$_2$—, —(CH$_2$)$_2$—, —Q—, —CH$_2$—Q— or —Q—CH$_2$— and Q is a heteroatom (including NH); either Y or Z are independently selected from —CH$_2$— and a heteroatom (including NH), or —Y—Z— is —CH=CH—, —CH=N— or —N=CH—; and R$_n$ is absent or represents one or more independently-selected substituents at any available position(s) on the X,Y,Z-containing ring. R$_1$ is H or alkyl; R$_2$ is H or a blocking group.

While (+)-4-aminocyclopent-2-ene-1-carboxylic acid is known, the present invention provides a new utility, i.e. its conversion to another compound of formula II, e.g. as a synthon.

DESCRIPTION OF THE INVENTION

Unsaturated lactams of formula I (in which —Y—Z— means —CH=CH—, —CH=N— or —N=CH—) can be prepared, by generally known means, by a Dieis-Alder reaction which comprises reacting a corresponding compound of formula III

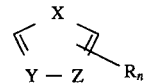

III with tosyl cyanide or chlorosulphonyl isocyanate. Depending on the nature of X, the compound of formula III may variously be, for example, a cyclopentadiene, 1,3-cyclohexadiene, furan, pyrrole or 1,2-dihydropyridine.

Unsaturated lactams of formula I may be reduced to give saturated lactams of formula I, if necessary with concomitant protection of susceptible groups, by known means. The unsaturated lactams may also be utilised in the preparation of compounds of the invention bearing one or more substituents R.

R$_n$ may be any substituent or substituents which do not interfere with the lactamase reaction; examples of R (if present) are methyl, ethyl, n-butyl, OH, Cl, Br, F, CF$_3$ and azido. For example, F or another halogen may be a substituent of X, e.g. as —CHHal—. The total number of carbon atoms in the group or groups R will not usually exceed 8. n may be, for example, 1 or 2, but R$_n$ is preferably absent.

The compound of formula III is preferably a 1,3-cyclohexadiene or, most preferably, a (symmetrical) 5-membered compound. X is preferably —CH$_2$—. Specific examples of compounds of formula I are the following:

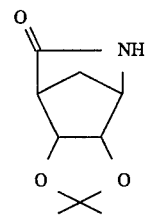

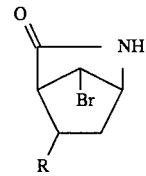

-continued

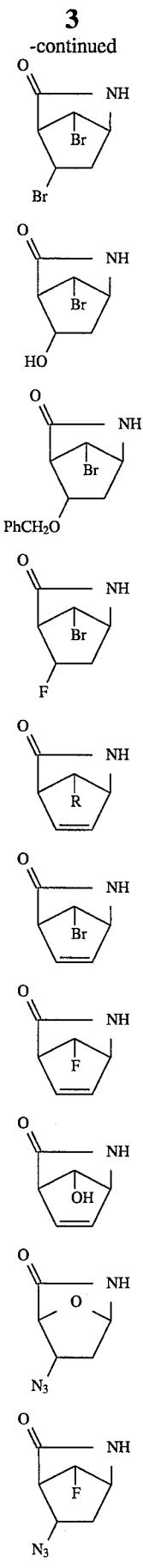

Others are given in PCT/GB90/00574.

It is surprising that material of biological origin will react selectively with a γ-lactam of formula I, to give the desired products in good yield. The material is described herein, for convenience, as a lactamase.

Suitable activities are those present in certain novel wild-type isolates of the genera Pseudomonas, Alcaligenes, Arthrobacter, Brevibacterium, Nocardia, Rhodococcus and Corynebacterium, whilst not being limited to isolates of these genera. Selection for these activities may be conducted in the presence of compounds containing one or more N-acyl substituents. If necessary, elevated levels of activity may be produced by growth of cells in the presence of such compounds. Particular examples of suitable activity are those produced maximally active in cells of the unique strains ENZA-20 and Rhodococcus sp ENZA-1, the latter when cultivated in a suitable medium in the presence of N-acetyl-L-phenylalanine or N-acetyl-D,L-phenylalanine.

Rhodococcus sp ENZA-1 was isolated from soil samples by enrichment culture in mineral salts medium containing N-acetyl-L-phenylalanine as the sole source of carbon and energy. The isolate has been deposited at the NCIMB in Aberdeen, on 17.10.89. The accession number is NCIMB 40213.

ENZA-20 was obtained from a sewage sample, and deposited at the NCIMB on 16.01.90. The accession number is NCIMB 40249.

Novel microorganisms have the ability to cause stereoselective formation of enantiomers of, say, 2-azabicyclo [2.2.1]hept-5-en-3-one and (−)-4-aminocyclopent-2-ene-1-carboxylic acid. The depos may, if desired, be subjected to conventional mutagenic/selection procedures, with a view to attaining improved effects.

The reaction of the lactam with the material having lactamase activity gives a compound of formula II which can be separated, as necessary or desired, from admixture with the unreacted lactam. If desired, the product ($R_2$=H) can be reacted with an acylating agent such as acetic anhydride, to give the corresponding compound (II: $R_2$= acyl). Other conventional N-blocking groups can be introduced as desired, examples being $CH_2Ar$, COOalk, CONHalk, $SO_2$alk, $Si(alk)_3$, CHO and COalk (alk meaning alkyl in its broadest sense).

If the lactamase reaction is conducted in the presence of water, $R_1$ is H. Alternatively, a nucleophile may be used to introduce an alkyl or other group $R_1$ directly. For example, the nucleophile is methanol.

(−)-4-Aminocyclopent-2-ene-1-carboxylicacid and other cis compounds of formula II are often the product of the process. If desired, racemic cis amino-acid may be converted to racemic cis/trans amino-acid which is then exterified, allowing ready separation. The, say, (+)-trans ester may be isolated.

One alternative synthesis of the amino-acids (II) is by cleavage of the racemic lactam (I) with a chiral nucleophile (e.g. an amine or alcohol). The cleavage may show some entantioselectivity, and the resultant diastereoisomers can be separated by fractional crystallisation. Acid hydrolysis (if needed) liberates the free amino-acid.

A further alternative comprises enantioselective reaction on the double bond. Potential examples are
(i) asymmetric hydroboration (as pioneered by H. C. Brown)
(ii) catalytic asymmetric dihydroxylation (B. Sharples)
(iii) binaphthyl rhodium/ruthenium-catalysed double bond displacement (Noyori; such a process is used in tonne scale menthol manufacture).

In each case, the unreacted lactam could be collected or the functional product be used to develop a route to a chiral drug.

Yet another alternative route to chiral products of the invention comprises conducting the Diels-Alder addition with a chiral Lewis acid catalyst or by using a chiral dienophile in place of tosyl cyanide. Economically, the use of a chiral catalyst is preferred. The resultant optically-enriched lactam may be subjected to the novel biotransformation process, in order to obtain a higher yield of pure (−)-lactam than may be possible from the racemate.

The optical isomers of the lactam (I) have a higher melting point than the racemate and therefore a higher lattice energy. Enantiomers may therefore be obtained by preferential crystallisation (entrainment), i.e. by seeding a supersaturated solution of racemate in a suitable solvent with pure enantiomer, such that more enantiomer is recovered than put in.

The following Examples illustrate the invention.

EXAMPLE 1

Preparation of Cells

Rhodococcus sp ENZA-1 was grown in a medium containing $KH_2PO_4$ (7 gl$^{-1}$), $Na_2HPO_4$ (2 gl$^{-1}$), $MgSO_4$ (0.4 gl$^{-1}$), NaCl (2 gl$^{-1}$) $CaCl_2.6H_2O$ (0.01 gl$^{-1}$), $FeCl_3.7H_2O$ (0.08 gl$^{-1}$), $ZnSO_4.7H_2O$ (0.0001 gl$^{-1}$), $(NH_4)_2SO_4$ (2 gl$^{-1}$) yeast extract (1 gl$^{-1}$) and glucose (10 gl$^{-1}$). The medium was adjusted to pH 7.0 with 5M NaOH and sterilised by autoclaving at 121° C. for 20 min. N-acetyl-L-phenyl-alanine at pH 7 was filter-sterilised and added to the cooled medium to give a final concentration of 10 gl$^{-1}$. The medium was distributed in 1 liter volumes within 5 liter shake flasks and 100 ml volumes within 500 ml shake flasks. A loopful from a slant of ENZA-1 was inoculated into 100 ml of the above medium and grown at 30° C. with shaking at 200 rpm, for 24 hours. A 5 liter shake flask was then inoculated with 50 ml of the seed culture and grown under the same conditions. The whole culture was then harvested after 48 hours growth, by centrifugation, and the cell paste was stored at −20° C. until use.

Preparation of Catalyst

Following thawing, Rhodococcus sp ENZA-1 cell paste (1.50 g) was suspended in phosphate buffer solution at pH 7 (0.1 M, 3.5 ml). The suspension of cells was then disrupted by sonication, to yield an essentially cell-free extract.

Preparation of (+)-lactam and (−)-amino-acid

The racemic lactam 2-azabicyclo[2.2.1]hept-5-en-3-one (218 mg, 2 mmol) was dissolved in phosphate buffer solution at pH 7 (0.1 M, 5.0 ml) and 0.5 ml of the cell-free extract was added. The resulting mixture was then inoculated at 30° C. with shaking for 14 days.

Isolation Of the (+)-lactam

The reaction mixture prepared above was extracted with dichloromethane (3×25 ml), and the organic layers were dried with anhydrous $MgSO_4$. Following filtration, the organic layers were concentrated by rotary evaporation at 30° C. at reduced pressure, to yield a white solid (110 mg) which was fractionated by chromatography on silica (5 g) in the presence of diethyl ether as the mobile phase, to give the (+)-lactam (97 mg, 0.9 mmol; 88% e.e.).

Derivation of the (−)-amino-acid and Isolation of the (−)-ester/amide

The aqueous layer resulting from dichloromethane extraction of the reaction mixture was acidified to pH 1 with dilute HCl (1M) and then concentrated to near dryness by rotary evaporation at 35° C. and reduced pressure. The resultant oil was then refluxed with benzene (25 ml) for 1 hour in a Dean-Stark apparatus to remove water. The resulting mixture was then concentrated by rotary evaporation at 35° C. and reduced pressure, to yield a brown solid which was refluxed with dry methanol (25 ml) for 5 hours. The resulting solution was then filtered and evaporated to dryness at 35° C. and reduced pressure. Dry pyridine (10 ml) was added, and the solution was cooled in an ice-bath. At this point, acetic anhydride (5 ml) was added dropwise with stirring, and the mixture was allowed to warm to room temperature. Following a further 2 hours stirring, the solution was concentrated by evaporation at 35° C. and reduced pressure. The resulting oil was then taken up in dichloromethane (150 ml) and washed consecutively with water (30 ml), sat. $NaHCO_3$ solution (2× 30 ml), dilute HCl (0.1 M, 2×30 ml) and brine (30 ml), at which point the solution was dried over anhydrous $MgSO_4$. Subsequently, the solution was concentrated by evaporation under reduced pressure at 35° C. and fractionated by chromatography on silica (10 g) in the presence of a mobile phase having the composition: $CH_2Cl_2$/$(CH_3)_2CO$ 80:20, to yield the (−)-ester/amide (II: X=$CH_2$; Y-Z=—CH=CH—; $R_1$= $CH_3$; $R_2$=Ac) (128 mg, 0.7 mmol; 81% e.e.).

EXAMPLE 2

The procedure of Example i was repeated, except that isolate ENZA-20 was used. In cell preparation, growth in the presence of N-acetyl-L-phenylalanine was not necessary. The products of reaction with the racemic lactam were the (−)-lactam and the (+)-amino-acid. The (−)-lactam had>98% e.e. The (+)-ester/amide was isolated.

We claim:

1. 2-Azabicyclo(2 2 1)hept-5-en-3-one, comprising predominantly the (+) enantiomer and a residual amount of the (−) enantiomer, wherein the (+) enantiomer is present in an enantiomeric excess of at least about 88% over the (−) enantiomer.

2. The 2-azabicyclo-[ 2.2.1]hept-5-en-3-one of claim 1, formed by a process comprising the steps of reacting a racemate of 2-azabicyclo(2.2.1)hept-5-en-3-one with an enzyme having lactamase activity or a microorganism having lactamase activity which stereoselectively cleaves the (−) enantiomer thereby forming the (−) enantiomer of 4-amino-cyclopent-2-ene-1-carboxylic acid or an ester thereof, and then isolating the 2-azabicyclo(2.2.1)hept-5-en-3-one having an enantiomeric excess of the (+) enantiomer.

3. The 2-azabicyclo(2.2.1)hept-5-en-3-one as claimed in claim 2, wherein the enzyme is used.

4. The 2-azabicyclo(2.2.1) hept-5-en-3-one as claimed in claim 2, wherein the microorganism is used.

5. The 2-azabicyclo(2.2.1)hept-5-en-3-one as claimed in claim 4, wherein the microorganism is Rhodococcus NCIMB 40213.

6. 2-Azabicyclo(2.2.1)hept-5-en-3-one, comprising predominantly the (−) enantiomer and a residual amount of the (+) enantiomer, wherein the (−) enantiomer is present in an enantiomeric excess of at least about 98% over the (+) enantiomer.

7. The 2-azabicyclo-(2.2.1 ) hept-5-en-3-one of claim 6, formed by a process comprising the steps of reacting a racemate of 2-azabicyclo(2.2.1)hept-5-en-3-one with an enzyme having lactamase activity or a microorganism having lactamase activity which stereoselectively cleaves the (+) enantiomer thereby forming the (+) enantiomer of 4-aminocyclopent-2-ene-1-carboxylic acid or an ester thereof, and then isolating the 2-azabicyclo(2.2.1)hept-5-en-3-one having an enantiomeric excess of the (−) enantiomer.

8. The 2-azabicyclo(2.2.1) hept-5-en-3-one as claimed in claim 7, wherein the enzyme is used.

9. The 2-azabicyclo(2.2.1)hept-5-en-3-one as claimed in claim 7, wherein the microorganism is used.

10. The 2-azabicyclo(2.2.1)hept-5-en-3-one as claimed in claim 9, wherein the microorganism is NCIMB 40249.

11. A composition comprising the (+) enantiomer of 2-azabicyclo(2.2.1)hept-5-en-3-one and the (-) enantiomer of 4-aminocyclopent-2-ene-l-carboxylic acid or an ester thereof-wherein [the] said (+) enantiomer is present in at least about 88% enantiomeric excess over the (−) enantiomer of 2-azabicyclo(2.2.1)hept-5-en-3-one.

12. The composition as claimed in claim 11, which is formed by reacting a .racemate of 2-azabicyclo( 2.2.1)hept-5-en-3-one with an enzyme having lactamase activity which stereoselectively cleaves the (−) enantiomer, thereby forming the (−) enantiomer of 4-aminocyclopent-2-ene-1-carboxylic acid or an ester thereof.

13. The composition as claimed in claim 11, which is formed by reacting a racemate of 2-azabicyclo(2.2.1)hept-5-en-3-one with a microorganism having lactamase activity which stereoselectively cleaves the (−) enantiomer, thereby forming the (−) enantiomer of 4-aminocyclopent-2-ene-1-carboxylic acid or an ester thereof.

14. The composition as claimed in claim 13, wherein the microorganism is Rhodococcus NCIMB 40213.

15. A composition comprising the (−) enantiomer of 2-azabicyclo(2.2.1)hept-5-en-3-one and the (+) enantiomer of 4-aminocyclopent-2-ene-1-carboxylic acid or an ester thereof, wherein said (−) enantiomer is present in at least about 98% enantiomeric excess over the (+) enantiomer of 2-azabicyclo(2.2.1)hept-5-en-3-one.

16. The composition as claimed in claim 15, which is formed by reacting a racemate of 2-azabicyclo(2.2.1)hept-5-en-3-one with an enzyme having lactamase activity which stereoselectively cleaves the (+) enantiomer, thereby forming the (+) enantiomer of 4-aminocyclopent-2-ene-1-carboxylic acid or an ester thereof.

17. The composition as claimed in claim 15, which is formed by reacting a racemate of 2-azabicyclo(2.2.1)hept-5-en-3-one with a microorganism having lactamase activity which stereoselectively cleaves the (+) enantiomer, thereby forming the (+) enantiomer of 4-aminocyclopent-2-ene-1-carboxylic acid or an ester thereof.

18. The composition as claimed in claim 17, wherein the microorganism is NCIMB 40249.

19. 2-Azabicyclo(2.2.1)hept-5-en-3-one, comprising predominantly the (−) enantiomer and a residual amount of the (+) anantiomer, wherein the (−) enantimoer is present in an ananiomeric excess of at least about 88% over the (+) enantiomer.

* * * * *